US007833016B2

(12) United States Patent
Gharib et al.

(10) Patent No.: US 7,833,016 B2
(45) Date of Patent: Nov. 16, 2010

(54) ROOT CANAL FILLING MATERIALS AND METHODS

(75) Inventors: Morteza Gharib, San Marino, CA (US); Erik Hars, Mission Viejo, CA (US)

(73) Assignee: Dentatek Corporation, Laguna Hills, CA (US)

( * ) Notice: Subject to any disclaimer, the term of this patent is extended or adjusted under 35 U.S.C. 154(b) by 0 days.

(21) Appl. No.: 11/752,812

(22) Filed: May 23, 2007

(65) Prior Publication Data

US 2007/0275353 A1 Nov. 29, 2007

Related U.S. Application Data

(60) Provisional application No. 60/802,662, filed on May 23, 2006.

(51) Int. Cl.
*A61C 5/02* (2006.01)
(52) U.S. Cl. .......................................... 433/224; 433/81
(58) Field of Classification Search .................... 433/81, 433/222.1, 224, 215, 226, 229; 600/424, 600/1–15
See application file for complete search history.

(56) References Cited

U.S. PATENT DOCUMENTS

| | | | | | |
|---|---|---|---|---|---|
| 3,318,000 | A | * | 5/1967 | Paris | 433/224 |
| 3,919,774 | A | * | 11/1975 | Fishman | 433/224 |
| 3,925,895 | A | * | 12/1975 | Kliment et al. | 433/224 |
| 4,063,561 | A | * | 12/1977 | McKenna | 128/207.15 |
| 4,652,257 | A | * | 3/1987 | Chang | 604/20 |
| 4,886,075 | A | * | 12/1989 | Jones | 607/134 |
| 5,660,817 | A | * | 8/1997 | Masterman et al. | 424/49 |
| 5,915,970 | A | * | 6/1999 | Sicurelli et al. | 433/220 |
| 6,183,253 | B1 | * | 2/2001 | Billet et al. | 433/81 |
| 6,734,795 | B2 | * | 5/2004 | Price | 340/572.1 |
| 2002/0022007 | A1 | * | 2/2002 | Gers-Barlag et al. | 424/59 |
| 2002/0058232 | A1 | * | 5/2002 | Weiss et al. | 433/224 |
| 2003/0124482 | A1 | * | 7/2003 | Calvert | 433/81 |
| 2004/0101809 | A1 | * | 5/2004 | Weiss et al. | 433/224 |
| 2004/0191729 | A1 | * | 9/2004 | Altshuler et al. | 433/215 |
| 2009/0047634 | A1 | | 2/2009 | Calvert | |

(Continued)

OTHER PUBLICATIONS

Innovative Bioceramix Inc, Iroot Sp Root Canal Sealer, FDA 510(k) Premarket Notification Summary, 510(k) No. K080917, dated Apr. 1, 2008.
Innovative Bioceramix Inc, Iroot Bioaggregate Root Canal Filling Material, FDA 510(k) Premarket Notification Summary, 510(k) No. K063422, dated Nov. 13, 2006.
Diadent. Diapex, FDA 510(k) Premarket Notification Summary, 510(k) No. K033585, dated Nov. 13, 2003.

(Continued)

*Primary Examiner*—Cris L Rodriguez
*Assistant Examiner*—Hao D Mai
(74) *Attorney, Agent, or Firm*—Knobbe, Martens, Olson & Bear, LLP

(57) ABSTRACT

In various embodiments of a method for filling root canal spaces, the root canal spaces are cleaned and irrigated, for example, by any suitable endodontic procedure, and the irrigating liquid is not removed from the canal spaces prior to filling. In some embodiments, a hydrophobic filler material is introduced into the root canal spaces while they are filled with liquid. As the canal spaces are filled, the hydrophobic filler material displaces the liquid and drives it out of the canal spaces, towards the crown of the tooth, where it can be removed. The hydrophobic filler material may comprise magnetically responsive particles having a hydrophobic surface coating that are compacted into the root canal spaces by application of a magnetic force field. In other embodiments, hydrophilic filler material in a flowable phase is introduced into the canal spaces where it partly displaces and partly absorbs the irrigating liquid before solidifying.

17 Claims, 5 Drawing Sheets

OTHER PUBLICATIONS

Coltene/Whaledent GMBH & CO., Guttaflow, FDA 510(k) Premarket Notification Summary, 510(k) No. K032662, dated Aug. 28, 2003.

Dentsply International, White MTA Material, FDA 510(k) Premarket Notification Summary, 510(k) No. K011009, dated Apr. 4, 2001.

Dentsply International, MTA Root Canal Sealer, FDA 510(k) Premarket Notification Summary, 510(k) No. K080203, dated Jan. 28, 2008.

Dentsply International, MTA Advanced Material, FDA 510(k) Premarket Notification Summary, 510(k) No. 073218, dated Nov. 20, 2007.

Dentsply International, MTA Material and MTA Material II, FDA 510(k) Premarket Notification Summary, 510(k) No. K981620, dated Jun. 6, 1998.

Dentsply International, AH Plus Root Canal Sealer, FDA 510(k) Premarket Notification Summary, 510(k) No. K960548, dated Feb. 8, 1996.

Essential Dental Systems Inc., EZ-Fill Xpress Epoxy Root Canal Cement System, FDA 510(k) Premarket Notification Summary, 510(k) No. K063856, dated Dec. 28, 2006.

Jeneric/Petron Inc., First Fill R.C.S., FDA 510(k) Premarket Notification Summary, 510(k) No. K011748, dated Jun. 6, 2001.

MDS, The Bi-Directional Spiral & Epoxy Root Canal Cement System, FDA 510(k) Premarket Notification Summary, 510(k) No. K992727, dated Aug. 13, 1999.

META Biomed Co. Ltd., Adseal Root Canal Sealer, FDA 510(k) Premarket Notification Summary, 510(k) No. K042769, dated Oct. 5, 2004.

META Biomed Co. Ltd., Metapaste, FDA 510(k) Premarket Notification Summary, 510(k) No. K032605, dated Aug. 25, 2003.

META Biomed Co. Ltd., Metapex, FDA 510(k) Premarket Notification Summary, 510(k) No. K032603, dated Aug. 25, 2003.

MPL Technologies Inc., Max-i-Probe Endodontic Sealer Delivery System, FDA 510(k) Premarket Notification Summary, 510(k) No. K971622, dated May 2, 1997.

Neo Dental Chemical Products Co. Ltd., Vitapex Pre-Loaded Dental Syringe, FDA 510(k) Premarket Notification Statement, 510(k) No. K973667, dated Sep. 25, 1997.

Parkell Inc., CZ-82000, FDA 510(k) Premarket Notification Summary, 510(k) No. K060946, dated Apr. 6, 2006.

Pentron Clinical Technologies, SE Epiphany Root Canal Sealant, Model N59SE, FDA 510(k) Premarket Notification Summary, 510(k) No. K060889, dated Mar. 31, 2006.

Pentron Laboratory Technologies, LLC., Fiberfill AGP, FDA 510(k) Premarket Notification Statement, 510(k) No. K023818, dated Nov. 15, 2002.

Pentron Laboratory Technologies, LLC., Fiberfill SGP, FDA 510(k) Premarket Notification Statement, 510(k) No. K023819, dated Nov. 15, 2002.

Pulpdent Corp., Pulpdent Calcium Hydroxide Preparation, FDA 510(k) Premarket Notification Summary, 510(k) No. K022734, dated Aug. 16, 2002.

Roeko Ulm Roescheisen GMBH & Co., Roeko Seal, FDA 510(k) Premarket Notification Summary, 510(k) No. K983037, dated Aug. 31, 1998.

Septodont S.A.S., Acroseal Root Canal or Apical Sealer, FDA 510(k) Premarket Notification Statement, 510(k) No. K023976, dated Nov. 27, 2002.

Sybron Dental Specialties Inc., Sealapex 4, FDA 510(k) Premarket Notification Summary, 510(k) No. K010940, dated Mar. 29, 2001.

Sybron Dental Specialties Inc., Kerr Modified Sealapex, FDA 510(k) Premarket Notification Summary, 510(k) No. K972369, dated Jun. 25, 1997.

Tulsa Dental Products Ltd., Mineral Trioxide Aggregate (MTA), FDA 510(k) Premarket Notification Summary, 510(k) No. K964174, dated Oct. 18, 1996.

Ultradent Products Inc., EndoREZ, FDA Premarket Notification Statement, 510(k) No. K042756, dated Oct. 4, 2004.

Vericom Co. Ltd., Well-Pex, FDA 510(k) Premarket Notification Summary, 510(k) No. K080266, dated Feb. 1, 2008.

Diadent, Material Safety Data Sheet for Diadent BioAggregate Root Canal Repair Material, dated Jan. 1, 2007.

Confi-Dental Products Co., Root Canal Filling Cement, available at http://www.confi-dental.com/home/DesktopModules/Pictures/PictureView.aspx?tabID=435&ProdID=247&mid=3171 in Product Profile, printed Jun. 29, 2009.

Confi-Dental Products Co., Material Safety Data Sheet for Root Canal Cement Powder, revision date Jul. 26, 2004.

Dentsply Maillefer, Densfil, Maillefer Densfil Frequently Asked Questions, available at http://www.maillefer.com/html/densfilfaq1.html,, printed Jun. 29, 2009.

Dentsply Maillefer, Densfil, Thermal Endodontic Obturation System, Product Information, printed Jun. 29, 2009.

Dentsply Maillefer, AH26/AH26 Silverfree Root Canal Sealing and Filling Materials, available at http://www.dentsply.es/DFU/eng/DFU__AH_26_eng.pdf, dated May 19, 1999.

Lightspeed USA, Simplifill, Lightspeed Product Information, available at http://www.lightspeedusa.com/productinfo.html, printed Jun. 30, 2009.

Discus Dental, Material Safety Data Sheet for Simplifill Points, dated Jun. 12, 2007.

"Endodontic Obturating System Simplifies Root Canals," RDH Magazine, available at http://www.rdhmag.com/display_article/228282/54/none/none/OnFea/Endodontic-obturating-system-simplifies-root-canals, dated May 20, 2005.

Ivoclar Vivadent, Apexit Plus Scientific Documentation, in 17 pages, dated Aug. 2005.

"Latest in Endodontics," Endodontology, Jun. 2004, pp. 30-31, vol. 16, Issue 1, Indian Endodontic Society, New Delhi, India, available online at http://medind.nic.in/eaa/t04/i1/eaat04i1c.shtml.

Meta Biomed Co. Ltd., Zinc Oxide-Based Root Canal Sealer, available at http://www.meta-biomed.com/english/dental/zobseal.html, printed Jun. 30, 2009.

Obtura Spartan, Resinate Resin Obturation System, available at http://www.obtura.com/5.26fnlresinatebro.pdf, dated 2006, printed Jun. 30, 2009.

Parkell Inc., Introducing MetaSEAL, available at http://www.parkell.com/pages/products/MetaSEAL.htm, printed Jun. 30, 2009.

Pentron Clinical Technologies, Resilon Obturation Material—The New Standard of Filling, available at http://www.pentron.com/pentron/admindocs/suggest_112.pdf, printed Jun. 30, 2009.

Pulpdent Corp., Pulpdent Root Canal Sealer, available at http://www.pulpdent.com/products/view/63, printed Jun. 30, 2009.

Roydent, Roydent Endodontic Products: Filling and Sealing materials: 2SEAL, available at http://www.roydent.com/prod_endo/html/prod_endo_fsm_2seal.htm, printed Jun. 30, 2009.

Sybron Dental Specialties Inc., Sealapex and Sealapex Xpress, available at http://www.sybronendo.com/index/sybronendo-fill-sealapex-xpress-02, printed Jun. 30, 2009.

Sybron Dental Specialties Inc., Tubli-Seal EWT and Tubli-Seal EWT Xpress from SybronEndo with Tubli-Seal and Tubli-Seal Xpress, available at http://www.sybronendo.com, printed Jun. 30, 2009.

Ultradent Products Inc., EndoREZ Accelerator, available at https://store.ultradent.com, printed Jun. 30, 2009.

GC America Inc, Nogenol Root Canal Sealer, available at http://www.gcamerica.com/nogenolroot.html, printed Jul. 1, 2009.

International Search Report and Written Opinion for International application No. PCT/US2007/012254, mailed Jul. 24, 2008.

International Preliminary Report on Patentability for International application No. PCT/US2007/012254, mailed Dec. 11, 2008.

Dentsply/Caulk, "Spectrum 800 Curing Light" product brochure, copyright 2002 Dentsply International.

\* cited by examiner

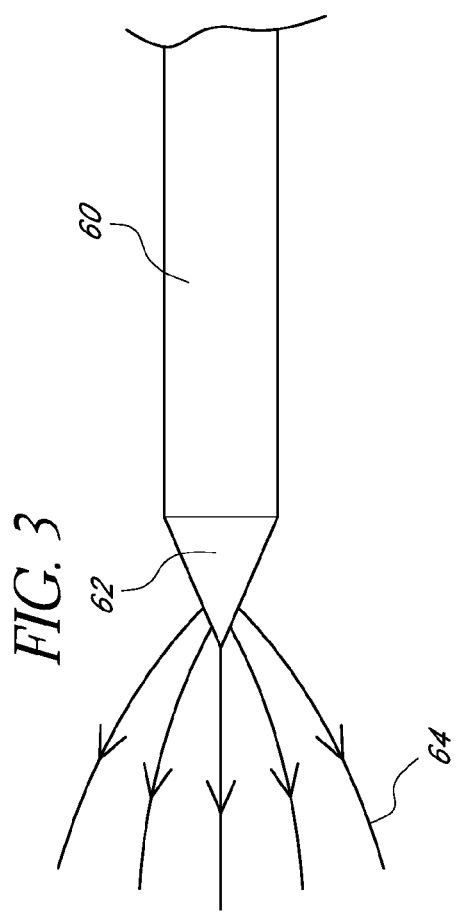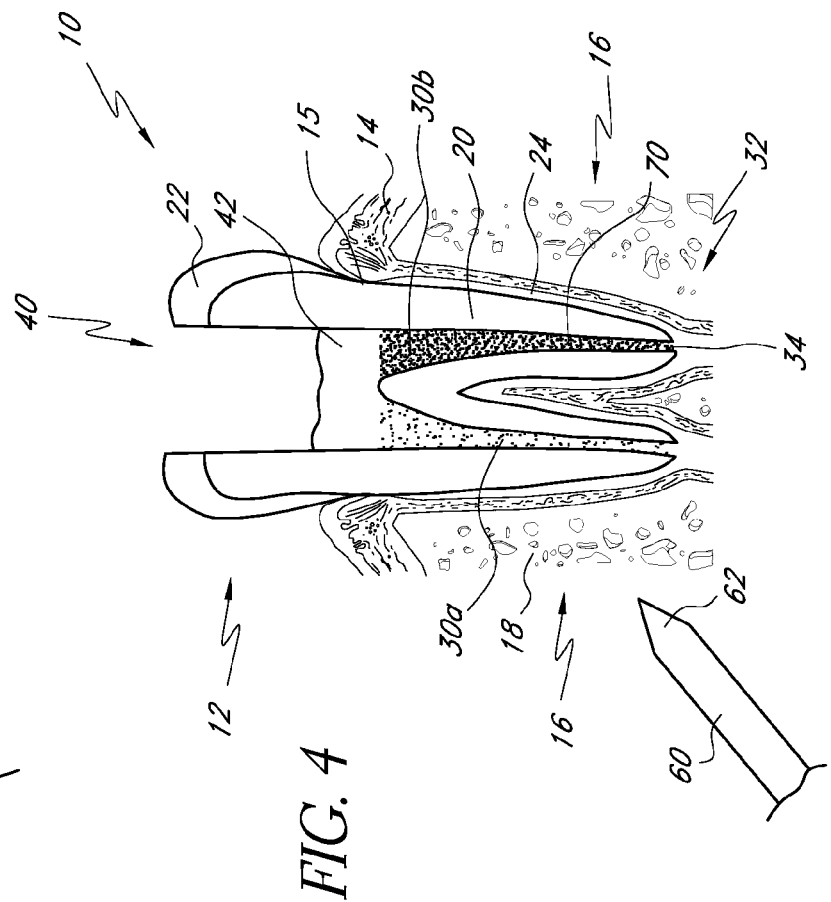

US 7,833,016 B2

ROOT CANAL FILLING MATERIALS AND METHODS

CROSS-REFERENCE TO RELATED APPLICATIONS

This application claims the benefit under 35 U.S.C. §119(e) of U.S. Provisional Patent Application No. 60/802,662, filed May 23, 2006, entitled "Root Canal Filling Materials and Methods," which is hereby incorporated by reference herein in its entirety.

BACKGROUND

1. Field

The present disclosure relates generally to filling spaces in a body location and more particularly to filling root canal spaces in a tooth.

2. Description of the Related Art

Treatment of root canal spaces in a tooth typically involves removal of organic material from the root canal spaces followed by filling the spaces with a filling material. Present filling materials are hydrophobic and may include gutta-percha, polymers, calcium hydroxide ($Ca(OH)_2$), and/or zinc oxide (ZnO) liners. Prior to filling the root canal spaces with these filling materials, the canal spaces typically must be widened, which is traditionally performed with hand- or machine-driven endodontic files. To ensure proper adhesion of the filling material to tooth dentin, moisture and fluids are evacuated from the canal spaces (such as by wicking or aspirating) prior to filling. Such evacuation of fluids commonly results in sucking organic components and contaminated fluids (e.g., pus, serum, and/or blood) from the apical periodontium through one or more canal orifices, which may cause re-infection of the canal spaces. Due to these and other deficiencies, the overall success rate for the treatment is around 70 percent. Because of the uncertainty and the cost of the process, extraction of the diseased tooth is often used as a treatment alternative.

SUMMARY

An embodiment of an apparatus comprises a manipulator which produces a non-contacting force field to manipulate a filling material during filling of a root canal space of a tooth. The filling material may comprise a plurality of particles responsive to the non-contacting force field. In some embodiments, the non-contacting force field may comprise a magnetic field.

An embodiment of a method for filling a root canal space of a tooth comprises using a non-contacting force field to manipulate a filling material during filling of the root canal space. In some implementations, the non-contacting force field comprises a magnetic field, and the filling material magnetically interacts with the magnetic field.

An embodiment of a method of filling a root canal system of a tooth comprises compacting colloidally suspended discrete particles in a root canal to fill the canal with a substantially solid filling.

An embodiment of a root canal filler for a tooth comprises a multiplicity of relatively large particles sized to form a plug in a canal space proximate an apex of the tooth and a multiplicity of relatively small particles sized to at least substantially fill the remainder of the canal space.

An embodiment of a method for filling a root canal space of a tooth comprises plugging a canal space proximate an apex of the tooth and subsequently at least substantially filling remaining space of the canal with a flowable filling material.

An embodiment of a hydrophilic root canal filling material is provided. The filling material may be adapted to be introduced into a root canal space when liquid is in the canal space during filling. The liquid may provide a barrier against migration of bacteria into an apical area of the tooth. When introduced into the root canal, at least a substantial portion of the liquid may be absorbed by the hydrophilic material.

An embodiment of a method of filling a root canal space of a tooth comprises introducing a hydrophobic material into a root canal space of a tooth when a liquid substantially fills the root canal space. The liquid may provide a barrier against migration of bacteria into an apical area of the tooth. The liquid may be substantially displaced from the root canal space by the hydrophobic material.

BRIEF DESCRIPTION OF THE DRAWINGS

FIG. 3 schematically illustrates an embodiment of a micromanipulator comprising a stylus having a magnetic tip. FIG. 3 schematically depicts example magnetic field lines near the tip.

FIG. 4 schematically illustrates a root canal filling method using the micromanipulator of FIG. 3 to magnetically guide magnetically responsive filler material into the canal spaces of a tooth.

DETAILED DESCRIPTION OF PREFERRED EMBODIMENTS

The present disclosure describes various materials and methods for endodontic treatments that overcome possible disadvantages associated with conventional root canal treatments. In certain embodiments of a method for filling root canal spaces, the root canal spaces are cleaned and irrigated (e.g., by any suitable endodontic procedure), and the irrigating liquid is not removed from the canal spaces prior to filling. In certain such embodiments, the method comprises introducing a hydrophobic filler material into the root canal spaces while they are filled with liquid (e.g., water). As the canal spaces are filled, the hydrophobic filler material displaces the liquid and at least partially drives the filler material out of the canal spaces, towards the crown of the tooth, as will be described more fully below.

In some embodiments, the hydrophobic filler material comprises a colloid of coated ferromagnetic particles (and/or other material that is responsive to a magnetic field). The coating advantageously may comprise a substantially hydrophobic substance. By way of example, the coating may comprise polyorganosiloxanes, polyorganosilanes, or mixtures thereof. For convenience, the magnetically responsive particles will be referred to hereinafter as "mag-particles."

Figure 1:
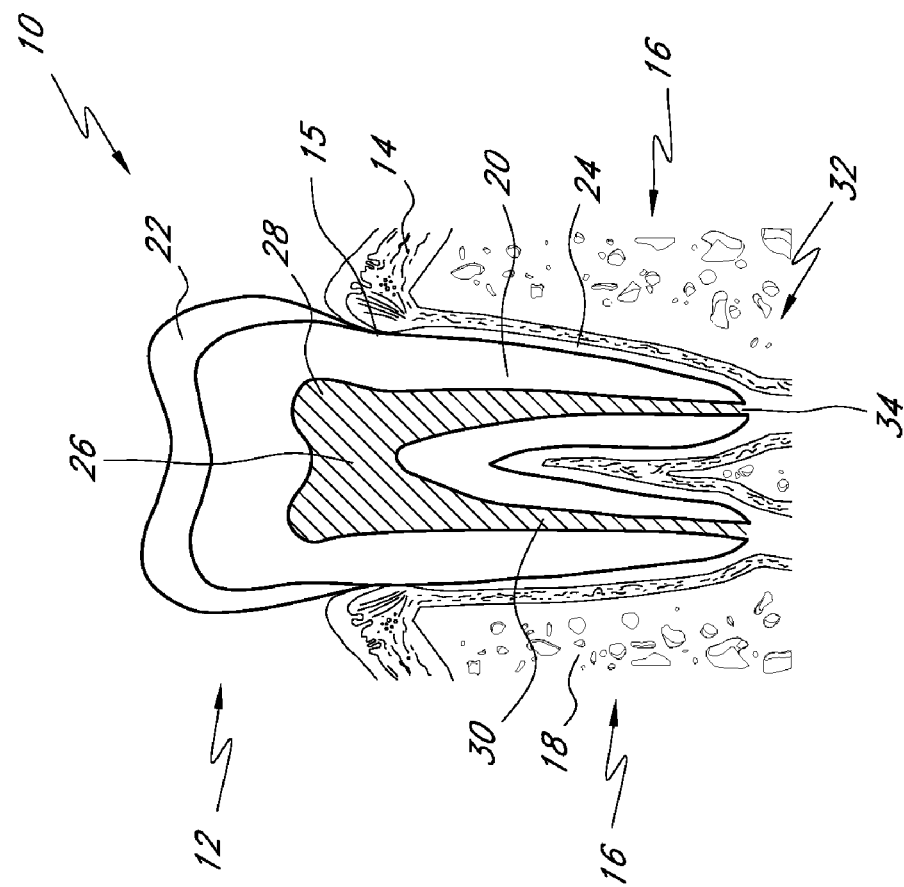
FIG. 1 is a cross section schematically illustrating a typical human tooth, which in this example is a molar.

FIG. 1 is a cross section schematically illustrating a typical human tooth 10, which comprises a crown 12 extending above the gum tissue 14 and at least one root 16 set into a socket (alveolus) within the jaw bone 18. Although the tooth 10 schematically depicted in FIG. 1 is a molar, the material and methods described herein may be used on any type of tooth such as an incisor, a canine, a bicuspid, or a molar. The hard tissue of the tooth 10 includes dentin 20 which provides the primary structure of the tooth 10, a very hard enamel layer 22 which covers the crown 12 to a cementoenamel junction 15 near the gum 14, and cementum 24 which covers the dentin 20 of the tooth 10 below the cementoenamel junction 15.

A pulp cavity 26 is defined within the dentin 20. The pulp cavity 26 comprises a pulp chamber 28 in the crown 11 and one or more root canal spaces 30 extending toward an apex 32 of each root 16. The pulp cavity 26 contains dental pulp, which is a soft, vascular tissue comprising nerves, blood vessels, connective tissue, odontoblasts, and other tissue and cellular components. The pulp provides innervation and sustenance to the tooth through the epithelial lining of the pulp chamber 26 and the root canal space 30. Blood vessels and nerves enter/exit the root canal space 30 through a tiny opening, the apical foramen 34, near a tip of the apex 32 of the root 16.

Figure 2A:
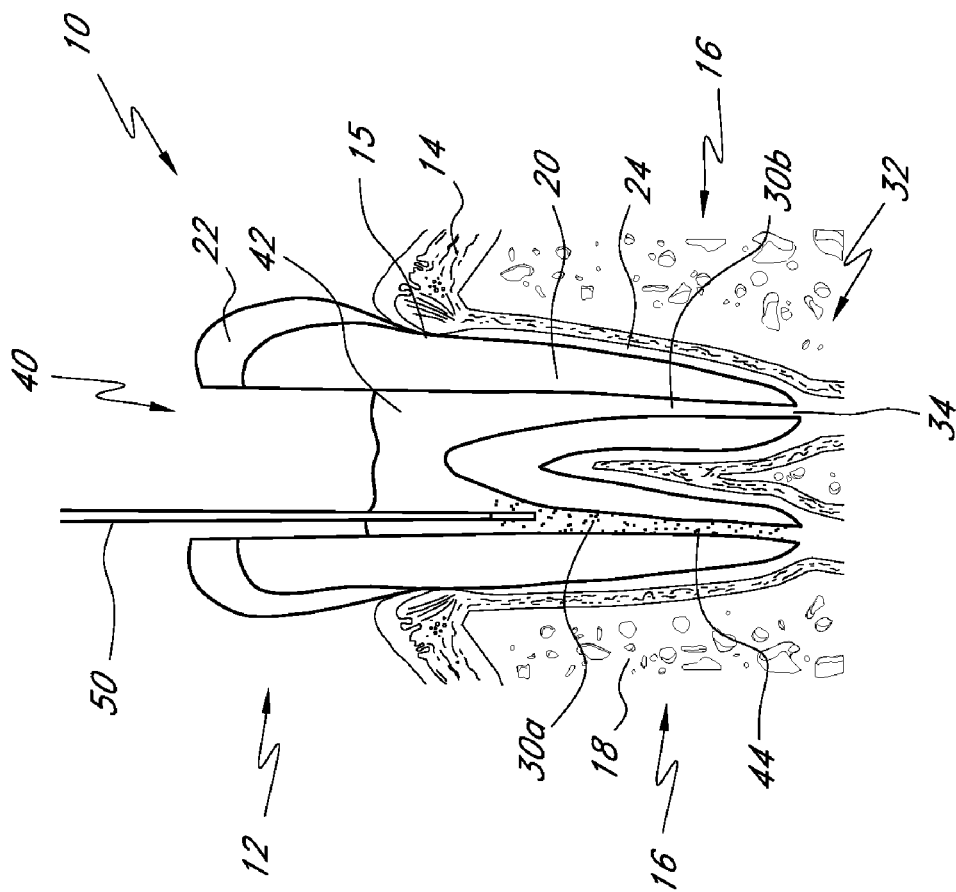
FIG. 2A schematically illustrates an embodiment of an endodontic treatment for filling the root canal spaces of the tooth.

FIG. 2A schematically illustrates one embodiment of an endodontic treatment for filling the canal spaces 30 of the tooth 10. A drill or grinding tool is initially used to make an opening 40 in the tooth 10. The opening 40 may extend through the enamel 22 and the dentin 20 to expose and provide access to pulp in the pulp cavity 26. The opening 40 may be made in a top portion of the crown 12 of the tooth 10 (as shown in FIG. 2A) or in another portion such as a side of the crown 12 or in the root 16 below the gum 14. The opening 40 may be sized and shaped as needed to provide suitable access to the pulp cavity 26 and/or all of the canal spaces 30. In some treatment methods, additional openings may be formed in the tooth 10 to provide further access to the canals 30 and/or to provide dental irrigation.

Figure 2B:
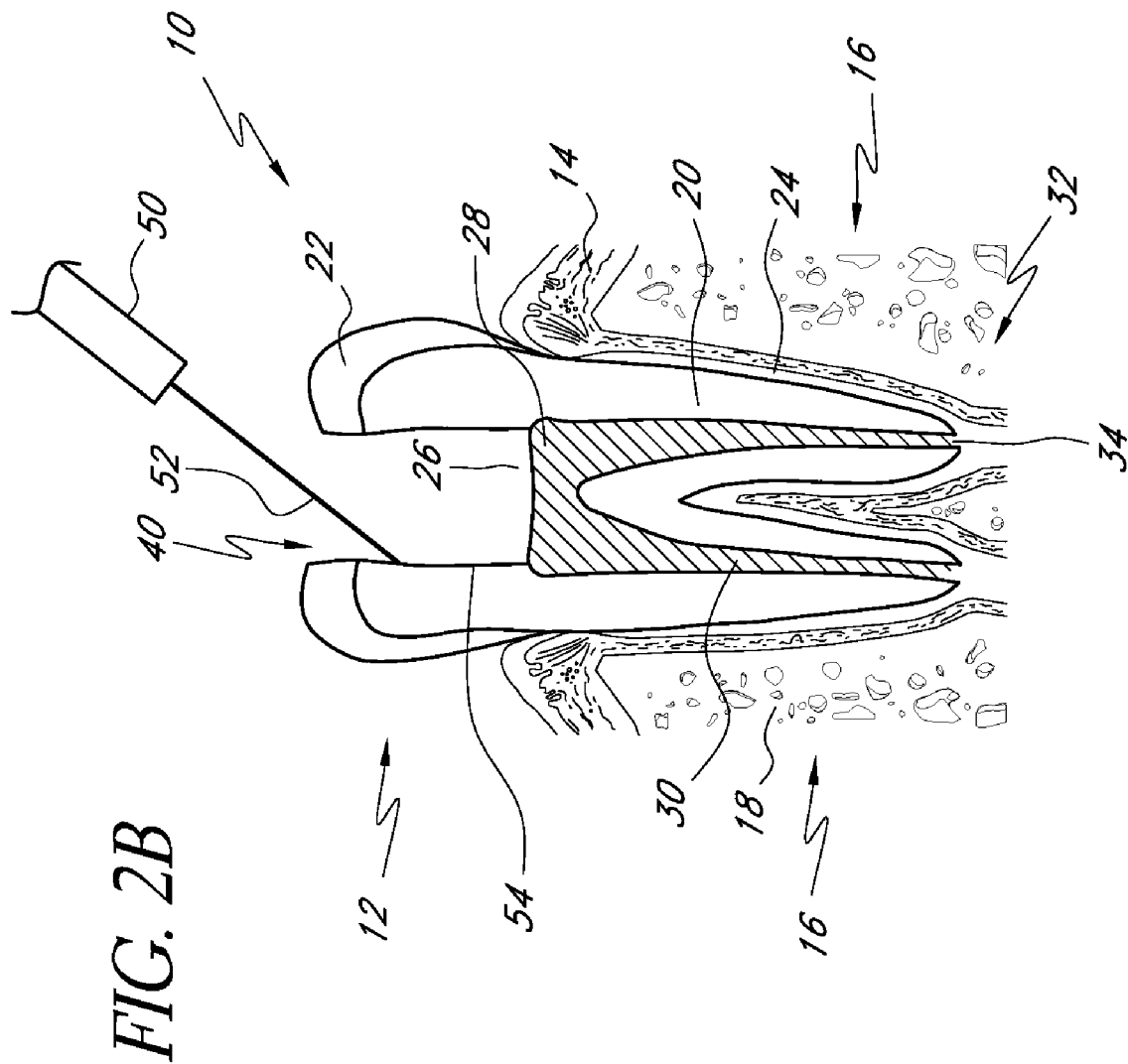
FIG. 2B is a cross-section view schematically showing an example endodontic method for cleaning a root canal system of a tooth, in which a high-velocity jet is directed toward a dentinal surface through an opening in the crown of the tooth.

The pulp cavity 26 and/or the canal spaces 30 may be cleaned and irrigated by any suitable method. For example, in some procedures, endodontic files are inserted into the root canal system to open the canal spaces 30 and remove organic material therein. An effective method for cleaning the root canal system is depicted in FIG. 2B, which schematically illustrates a high velocity collimated jet 52 of liquid (e.g., water) directed through the opening 40 toward a dentinal surface 54 of the tooth 10. In some embodiments, the high-velocity liquid jet may have a velocity in a range from about 50 m/s to about 300 m/s and may have a transverse size (e.g., diameter) in a range from about 1 micron to about 1000 microns.

Impact of the jet 52 causes acoustic energy to propagate from the impact site on the dentinal surface 54 through the entire tooth 10, including the root canal system. The acoustic energy is effective at detaching substantially all organic material in the root canal system from surrounding dentinal walls. The acoustic energy may be effective at cleaning the root canal system, because the acoustic energy generates acoustic cavitation effects (e.g., cavitation bubbles, cavitation jets, acoustic streaming, entrainment, etc.), which efficiently detach and/or delaminate organic material from dentinal surfaces and tubules. The treatment time during which the high-velocity jet 52 is directed toward the tooth 10 may range from about 1 second to about 120 seconds in various cleaning methods.

In many embodiments, the detached organic material can be flushed from the root canal using an irrigation fluid (e.g., water). In some embodiments, liquid from the high-velocity jet provides the irrigation fluid. In other embodiments, a low-velocity jet or stream provides the irrigation fluid. The liquid jet 52 may be directed from a handpiece 50 that can be manipulated within a patient's mouth by a dental practitioner. In certain endodontic procedures, the high velocity liquid jet 52 is directed into the pulp cavity 26 and/or the root canal spaces 30 to excise and/or emulsify organic material therein. The liquid jet 52 may be generated by a high pressure compressor system or by a pump system in various embodiments. Further details of apparatus and methods for generating the high velocity jet 52 and using the jet 52 to clean root canal systems are found in U.S. patent application Ser. No. 11/737,710, filed Apr. 19, 2007, entitled "Apparatus and Methods for Treating Root Canals of Teeth," which is hereby incorporated by reference herein in its entirety.

In certain preferred embodiments, after cleaning the canal spaces 30, irrigating liquid 42 (e.g., water) is not removed from the canal spaces 30 prior to filling. The irrigating liquid 42 advantageously may act as a vector for any floating particles and/or organic material and as a barrier against the influx of periapical fluid (e.g., through the apical opening 34). Filling material 44, such as the hydrophobic filling material described herein, may then be applied to the canal spaces 30. As the canal spaces 30 are filled, the hydrophobic filler material 44 displaces the irrigating liquid 42 and forces the liquid 42 at least partially out of the canal spaces 30, toward the opening 40 in the crown 12 of the tooth 10 (or toward any other suitable opening formed in the tooth 10).

In certain embodiments, the filler material 44 comprises a sterile colloid comprising mag-particles. The filler material 44 may be provided to a dental practitioner in standard 1.8 milliliter dental cartridges. In a preferred embodiment schematically illustrated in FIG. 2A, the colloid is applied to the canal spaces 30 using a standard cartridge syringe with an injection needle 50 such as, for example, a sterile disposable 30-gauge short injection needle. In some procedures, the colloid is applied into the canal spaces 30 without pressure and without binding the injection needle 50 to the walls of the canal space 30, which advantageously may reduce application of pressure to the liquid 42 present in the canal space 30 and may allow the liquid 42 to be displaced from and escape the canal space 30. In the example method depicted in FIG. 2A, the needle 50 has been used to apply the filler material 44 to a portion of the canal space 30a. After filling the canal space 30a, the dental practitioner may fill other spaces in the tooth 10, such as the canal space 30b. Although depicted as straight in FIG. 2A, the needle 50 may be bent and/or curved to access portions of the canal spaces 30a, 30b. In some embodiments, portions of the needle 50 may be flexible.

In certain embodiments, a force field is used to manipulate the filler material during the filling of the canal spaces 30. The force field advantageously may be a non-contacting force field that applies a force to the filler material without physically contacting the material. For example, the force field may comprise a magnetic force field, and the filler material may comprise a substance that is responsive to the magnetic force field.

As schematically illustrated in FIG. 3, the magnetic force field may be applied using a micromanipulator comprising a stylus 60 having a magnetic tip 62. FIG. 3 schematically depicts example magnetic field lines 64 near the tip 62. In other embodiments, the magnetic field lines 64 may have a different configuration and/or polarity than shown in FIG. 3. For example, the magnetic field lines 64 may have a configuration that includes components such as dipole, quadripole, and/or higher order multipole components. In some methods for filling root canal spaces, the magnetic tip 62 of the stylus 60 is positioned near the tooth 10 and moved toward the apex 32 adjacent to the tooth root 16. FIG. 4 schematically illustrates application of the tip 62 of the stylus 60 to the canal space 30*a* of the tooth 10. The magnetic tip 62 may be moved toward the apex 32 one or more times during a treatment. The magnetic field of the tip 62 may provide an attractive force that urges the mag-particles in the canal space 30*a* towards the apex 32 until substantially all the canal space 30*a* is filled, and the mag-particles are condensed in the canal space 30*a*. As the mag-particles are condensed, the liquid 42 in the canal spaces 30 is squeezed outward due to the hydrophobic surface property of the coating material of the mag-particles. This procedure may be repeated for the canal space 30 in each root 16 of the treated tooth 10. Surplus colloid can be removed from the access opening 40 and coronal pulp chamber 28.

In some methods, the mag-particles are also condensed in the canal spaces 30 using an endodontic spreader such as, for example, a No. 1 dental hand-spreader and/or plugger (e.g., a Schilder spreader) so as to form a substantially solid core 70 of mag-particles in the canal spaces. The substantially solid core 70 is schematically illustrated in the canal space 30*b* shown in FIG. 4. The resulting core 70 advantageously may be substantially bacterio-static, substantially tissue compatible, and not substantially affected by tissue metabolism. The core 70 of mag-particles also may be substantially radio-opaque. The filled canal spaces 30 may be sealed over in a conventional manner, such as with a bonded restorative material.

In certain preferred embodiments, mag-particles of different sizes are used in the filling process. In order to reduce the likelihood that mag-particles migrate through the apical opening 34 of the tooth 10 into surrounding vascularized tissue, larger mag-particles may be introduced first into the canal spaces 30, followed by introduction of smaller mag-particles. The larger mag-particles advantageously may have a size that allows the mag-particles to migrate proximate to the apical opening 34, but not through the apical opening 34. The magnetic tip 62 of the stylus 60 may be used to assist condensing the larger and/or the smaller mag-particles in the canal spaces 30. In certain embodiments, the mag-particle coating is somewhat compliant such that the coatings can deform as magnetic attraction from the stylus 60 pulls them through the root canal towards the apex 32 and into progressively smaller spaces. It is beneficial if the coating is not so compliant as to deform to a size smaller than that of the apical opening 34 (typically, 30 microns). As an example, in certain embodiments, the size of the larger mag-particles may be in a range from about 35 to about 200 microns, more preferably in a range from about 40 to 100 microns, and even more preferably in a range from about 50 to 70 microns. The larger mag-particles may thus advantageously be used to form a plug in a portion of the root canal space 30 adjacent the apex 32 of the tooth 10. The mag-particles forming the plug may be compacted using the magnetic field of the stylus 60 and may bond to each other by diffusion of the coating material.

In certain preferred embodiments, following creation of the plug comprising the larger mag-particles, smaller size mag-particles are introduced into the canal spaces 30. By way of example, the size of the smaller mag-particles may be in a range from about 2 to 30 microns, more preferably in a range from about 2 to 15 microns, and even more preferably in a range from about 2 to 5 microns. In certain such preferred embodiments, the mag-particles are sufficiently small to readily fill the small side canals, fins, and narrow spaces that typically extend laterally from the main root canal spaces 30. In some methods, the smaller mag-particles are compacted by means of the magnetic field and bond to each other by diffusion of the coating materials, thereby creating a rigid volume of filling material that fills the root canal system.

Various micromanipulators may be utilized to magnetically guide the mag-particles to targeted sites using magnetic force fields. Embodiments of the micromanipulator may use a magnetic force to guide the mag-particles by application of an attractive force, a repulsive force, and/or a combination thereof to pull and/or to push the mag-particles toward the targeted sites. In some embodiments, the micromanipulator is configured to provide a suitable magnetic force gradient to guide the mag-particles. By way of example, the micromanipulator may comprise a stylus (such as the stylus 60 described above) having a tip 62 that comprises one or more magnets or electromagnets. The one or more magnets may comprise rare earth (e.g., neodymium) magnets. In another embodiment, the micromanipulator comprises a plurality of coils forming a matrix of electromagnets. When suitably energized, the electromagnetic matrix of coils creates temporal and/or spatial electromagnetic field variations (statically or dynamically) to provide electromagnetic field patterns and field gradients that increase or optimize the force (and/or force gradient) applied to the mag-particles. The force gradient may be used to control the degree of mag-particle compactness and also to prevent the filler material 44 from reaching unwanted areas (e.g., the apical opening 34).

In certain treatment embodiments, some of the mag-particles are guided by the micromanipulator to assist moving surrounding filling material into small cracks, holes, crevices, channels, and/or spaces in the root canal system. For example, movement of the mag-particles may cause some of the surrounding fluid and/or filler material to flow due to a coupling force between the mag-particles and the fluid and/or filler material. The coupling force may comprise, for example, friction, viscosity, etc. In some methods, a time varying force field (and/or force gradient) is applied to the mag-particles to cause such a flow. The fluid motions induced by the movement of the mag-particles may assist introduction of filler material into the smaller root canal spaces.

Figure 5:
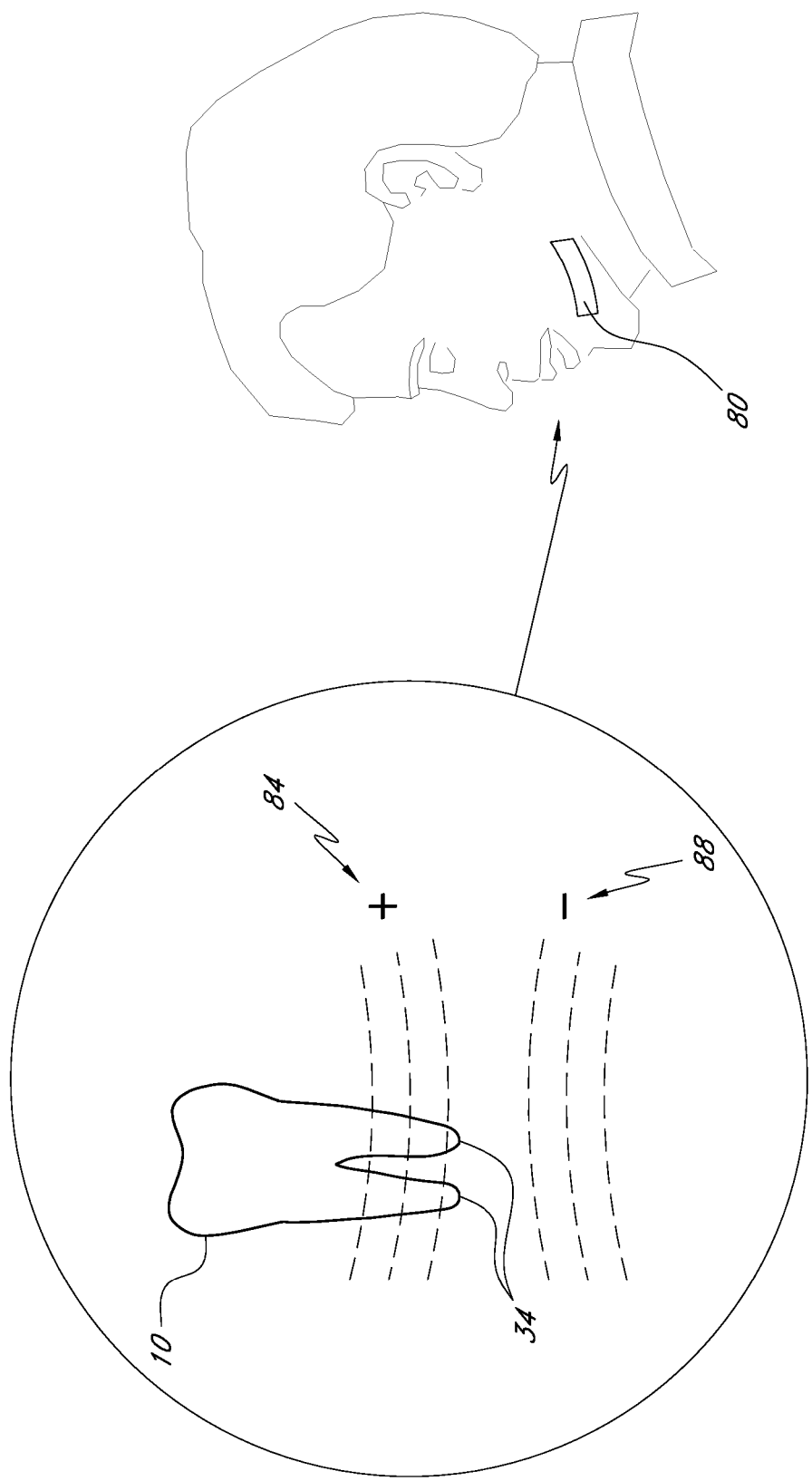
FIG. 5 schematically illustrates another embodiment of a filling method using a matrix of electromagnetic coils to produce a magnetic field gradient near a tooth (shown in the inset).

In some embodiments, the electromagnetic matrix is in the form of a strip 80 that is mounted on the head of the patient with the electromagnetic matrix in proximity to the apex of the tooth or teeth under treatment, as illustrated schematically in FIG. 5. The matrix may be powered by a power-supply that is controlled by a computer or microprocessor. The power supply drives the matrix of coils selectively under the control of computer software to create a magnetic-field gradient in the manner of a magnetic phased array. As schematically depicted in FIG. 5, the magnetic field gradient may be configured to provide a positive region 84 of attractive magnetic field to the root canal system, while providing a negative region 88 of zero or repulsive magnetic field near the apical openings 34 of the tooth 10 under treatment. The matrix may be spatially calibrated to the location of the apical openings 34, so that the field gradient generated by the matrix is precisely located with respect to the tooth 10 under treatment and draws the mag-particles through the canal system, but not through the apical openings 34. Accordingly, the electromagnetic matrix may preferably be attached to the patient in a manner that prevents or inhibits relative motion between the matrix and the tooth 10 under treatment when the magnetic field is applied. Such attachment may be accomplished by means of a helmet (e.g., for upper teeth), a jaw clamp (e.g., for lower teeth), or by clamping the matrix to one or more teeth adjacent the tooth 10 under treatment.

The matrix of coils may be used not only to move the mag-particles, but also to sense movement of the mag-particles. For example, as the mag-particles fill the root canal system, the mag-particles will cross magnetic field lines produced by the matrix, which generates a direct current (DC) in the coils. By measuring the DC current (and/or voltage) in each coil, relative movement between the mag-particles and the tooth 10 under treatment may be calculated. In some embodiments, the relative motion of the mag-particles is output on a display for viewing by the dental practitioner. In such embodiments, the dental practitioner may observe in real-time the migration of the mag-particles into the root canal system and the mag-particles' location relative to the apical openings 34. To provide increased control over the filling treatment, the magnetic field intensity, gradient, spatial and/or temporal configuration may be altered in accordance with the sensed movement. In an alternative embodiment, the matrix of coils provides a low intensity field for sensing movement without moving the particles, and the magnetic field that moves the particles is applied by a micromanipulator such as a handheld stylus manipulated by the dental practitioner (e.g., the stylus 60 shown in FIG. 3).

In some methods, after the filler material 44 comprising the mag-particles has sufficiently cured, energy is applied to heat the filler material 44 above the melting point to at least partially liquefy the filler material 44 and/or the mag-particles. The applied energy may comprise electric, magnetic, and/or electromagnetic energy such as, for example, from an applied electric field and/or magnetic field. In some embodiments, the applied energy comprises electromagnetic energy (e.g., ultrasound). The at least partially liquefied material may then solidify into a substantially solid core within the root canal system of the treated tooth.

In some cases, it may be desirable for the substantially solid core of mag-particles to be removed (e.g., for re-treatment of the tooth 10). In some treatment methods, the core may be at least partially liquefied by application of energy to the affected tooth. As described above, the applied energy may comprise electric, magnetic, and/or electromagnetic energy. For example, ultrasound energy may be applied, e.g., with a Cavitron® instrument available from Dentsply International, York, Pa. The liquefied core material can be suctioned or irrigated out of the canal spaces 30.

In other embodiments of methods for filling root canal spaces, the filling material may comprise a hydrophilic material such as, for example, a protein-based, reversible hydrocolloid. Protein-based reversible hydrocolloids are thermoplastics, which may liquefy in a temperature range above about 80 to 95 degrees centigrade and may solidify in a temperature range below about 40 to 45 degrees centigrade. Liquefaction and solidification temperature ranges may be different in different hydrocolloids. When in a liquid phase, reversible hydrocolloids may be able to absorb several times their volume of water. To avoid substantial changes in the physical properties of the hydrocolloid, in some methods water absorption is limited to about 30% of the volume of the hydrocolloid. Advantageously, the filling material may further comprise at least one bacterio-static substance, as well as at least one substance to provide radio-opacity. The filling material may comprise both a hydrophobic material (e.g., mag-particles) and a hydrophilic material (e.g., a reversible hydrocolloid) in some embodiments.

In certain method embodiments, the hydrophilic filling material is supplied in sealed 1.8 ml dental cartridges suitable for use in dental syringes. To liquefy the filling material, the cartridges may be placed in a heated liquid (e.g., hot or boiling water) for a liquefaction time that is about 10 minutes for some hydrocolloids. After the filling material is sufficiently liquefied, the cartridge can be placed in a cartridge syringe fitted with a suitable needle, for example, a 30 gauge short needle.

To deliver the filling material to the root canal system, the needle may be curved and/or bent to access the canal spaces 30 in the tooth 10 under treatment. In certain preferred embodiments, the needle is placed without binding into the canal space 30, and a suitable amount of liquefied filling material is injected into the space 30 to partially absorb and/or partially displace liquid in the canal space 30. It may be desirable in some embodiments for enough water from the canals 30 to be displaced such that no more than about 30% of the water is absorbed by the hydrocolloid filler (e.g., at least about 70% of the water is displaced). By introducing a suitable amount of liquid reversible hydrocolloid into the canal spaces 30, the hydrocolloid may help maintain the liquid stage of filler material previously introduced into the canal spaces 30, may help maintain application of pressure, and thereby may help transport the filler material to the apex 32 and to substantially all the canal spaces 30 before the filler material solidifies. The filled canal spaces 30 may be sealed over in a conventional manner with a bonded restorative material.

As described above, in some methods, after the filler material has sufficiently cured, energy is applied to heat the filler material toward or above the melting point to at least partially liquefy the filler material (and/or mag-particles if used). The at least partially liquefied material may help fill the canal spaces 30 and may help provide a substantially uniform core of material in the root canal system. The applied energy may comprise electric, magnetic, and/or electromagnetic energy such as, for example, from an applied electric and/or magnetic field. In some embodiments, the applied energy comprises electromagnetic energy (e.g., ultrasound). The at least partially liquefied material may then solidify into a substantially solid core within the root canal system of the treated tooth.

Although the tooth 10 depicted in the figures is a molar, one of ordinary skill in the art will appreciate that the procedures may be performed on any type of tooth such as an incisor, a canine, a bicuspid, or a molar. Also, the disclosed methods are capable of filling root canal spaces having a wide range of morphologies, including highly curved root canal spaces which are difficult to fill using conventional dental techniques. Moreover, the disclosed methods may be performed on human teeth (including children's teeth) and/or on animal teeth.

The foregoing description sets forth various preferred embodiments and other illustrative but non-limiting embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method/process may be performed in any suitable sequence and are not necessarily limited to any particular disclosed sequence. Accordingly, the scope of each of the inventions disclosed herein is to be determined according to the following claims and their equivalents.

What is claimed is:

1. A system for filling a root canal space of a tooth, the system comprising:
a filling material comprising a plurality of particles responsive to a non-contacting force field, said filling material configured to at least partially fill a root canal space of a tooth; and
a manipulator configured to produce the non-contacting force field and to manipulate the filling material without physically contacting the filling material during filling of the root canal space of the tooth, the non-contacting force field comprising a magnetic field, the manipulator configured to be positionable near the tooth and to provide a sufficient non-contacting force to compact at least some of the filling material toward an apex in the root canal space.

2. The system of claim 1, wherein the manipulator comprises one or more magnets or electromagnets.

3. The system of claim 1, wherein the plurality of particles comprises particles having a ferromagnetic core substantially surrounded with a hydrophobic coating.

4. The system of claim 3, wherein the hydrophobic coating comprises polyorganosiloxanes, polyorganosilanes, or a mixture thereof.

5. The system of claim 1, wherein the manipulator is configured to be handheld.

6. The system of claim 1, wherein the manipulator is configured to be mounted to the tooth, a jaw, or the head of a patient.

7. A method for filling a root canal space of a tooth, comprising:
filling a portion of a root canal space of a tooth with a filling material responsive to a non-contacting force field;
positioning a manipulator near a root of the tooth, the manipulator configured to provide the non-contacting force field through dentinal tissue in the root of the tooth without being in physical contact with the filling material during application of the non-contacting force field; and
applying the non-contacting force field to the filling material with the manipulator to move at least some of the filling material in the root canal space.

8. The method of claim 7, wherein the non-contacting force field comprises a magnetic field and the filling material magnetically interacts with the magnetic field.

9. The method of claim 7 wherein applying the non-contacting force field comprises:
moving the manipulator along the root of the tooth toward an apex of the tooth to urge at least some of the filling material toward the apex.

10. The method of claim 9, wherein applying the non-contacting force field further comprises using the non-contacting force field of the manipulator to compact the filling material in the root canal space.

11. The method of claim 7, wherein the manipulator is configured to be handheld.

12. A method for filling a root canal space of a tooth, comprising:
filling a portion of the root canal space of the tooth with a filling material responsive to a non-contacting force field, said filling the portion of the root canal space comprising:
filling at least a first portion of the root canal space with a first filling material comprising a first plurality of particles responsive to the non-contacting force field, the first plurality of particles having a first size; and
filling at least a second portion of the root canal space with a second filling material comprising a second plurality of particles responsive to the non-contacting force field, the second plurality of particles having a second size, the second size smaller than the first size;
positioning a manipulator near the tooth, the manipulator configured to provide the non-contacting force field without being in physical contact with the filling material during application of the non-contacting force field; and
applying the non-contacting force field to the filling material with the manipulator.

13. The method of claim 12, wherein the first portion of the root canal space is proximate an apex of the tooth.

14. The method of claim 13, wherein the second portion of the root canal space comprises substantially the remainder of the root canal space.

15. The method of claim 12, wherein the first size is selected to be larger than an apical opening of the tooth.

16. The method of claim 12, wherein the first size is in a range from about 35 microns to about 200 microns and the second size is in a range from about 2 microns to about 30 microns.

17. The method of claim 12, wherein the first plurality of particles comprises particles having a ferromagnetic core substantially surrounded with a hydrophobic coating, the non-contacting force field comprises a magnetic field, and applying the non-contacting force field comprises urging at least a portion of the first plurality of particles toward an apex of the tooth with the magnetic field to form a plug adjacent the apex of the tooth.

* * * * *